United States Patent [19]

Gordon

[11] 4,215,198

[45] Jul. 29, 1980

[54] STERILITY TESTING UNIT

[76] Inventor: Maurice R. Gordon, 15 Stuyvesant Cir. W., South Setauket, N.Y. 11733

[21] Appl. No.: 942,612

[22] Filed: Sep. 15, 1978

[51] Int. Cl.² .............................................. C12Q 1/22
[52] U.S. Cl. ...................................... 435/31; 435/311
[58] Field of Search ................ 195/103.5 M, 127, 139; 210/94, 136, 321 R, 337, 338; 435/31, 311

[56] References Cited

U.S. PATENT DOCUMENTS

| 2,672,431 | 3/1954 | Goetz | 195/103.5 M X |
|---|---|---|---|
| 2,761,813 | 9/1956 | Goetz | 195/103.5 M X |
| 3,448,011 | 6/1969 | Russomanno | 195/103.5 M X |
| 3,741,877 | 6/1973 | Shaufus et al. | 195/127 |
| 3,969,241 | 7/1976 | Skrabak et al. | 210/337 |
| 4,036,698 | 7/1977 | Bush et al. | 195/127 X |
| 4,066,512 | 1/1978 | Lai et al. | 195/127 |
| 4,092,221 | 5/1978 | Schlichting | 195/127 |
| 4,139,469 | 2/1979 | Rainin et al. | 210/136 |

OTHER PUBLICATIONS

"Falcon Sterile Disposable Filters", Bector, Dickinson & Co., pp. 1–4.
Arthur Thomas Laboratory Apparatus, Catalog Supplement, vol. 2, No. 2, Summer 1978, No. 4619-D12, D22.
"Sartorius Membranfilter, Sterility Testing System", Sartorius Filters Inc., Catalog SE0 5682.
Millipore Sterility Testing Systems, Catalog No. XX2504700, 35, 37 and 57, Millipore Steritest System, Brochure PB432.

Primary Examiner—R. B. Penland
Attorney, Agent, or Firm—Brumbaugh, Graves, Donohue & Raymond

[57] ABSTRACT

A stackable disposable filtration-incubation unit for testing the sterility of filterable liquids which can be sealed using internal means and methods for carrying out the sterility tests.

5 Claims, 7 Drawing Figures

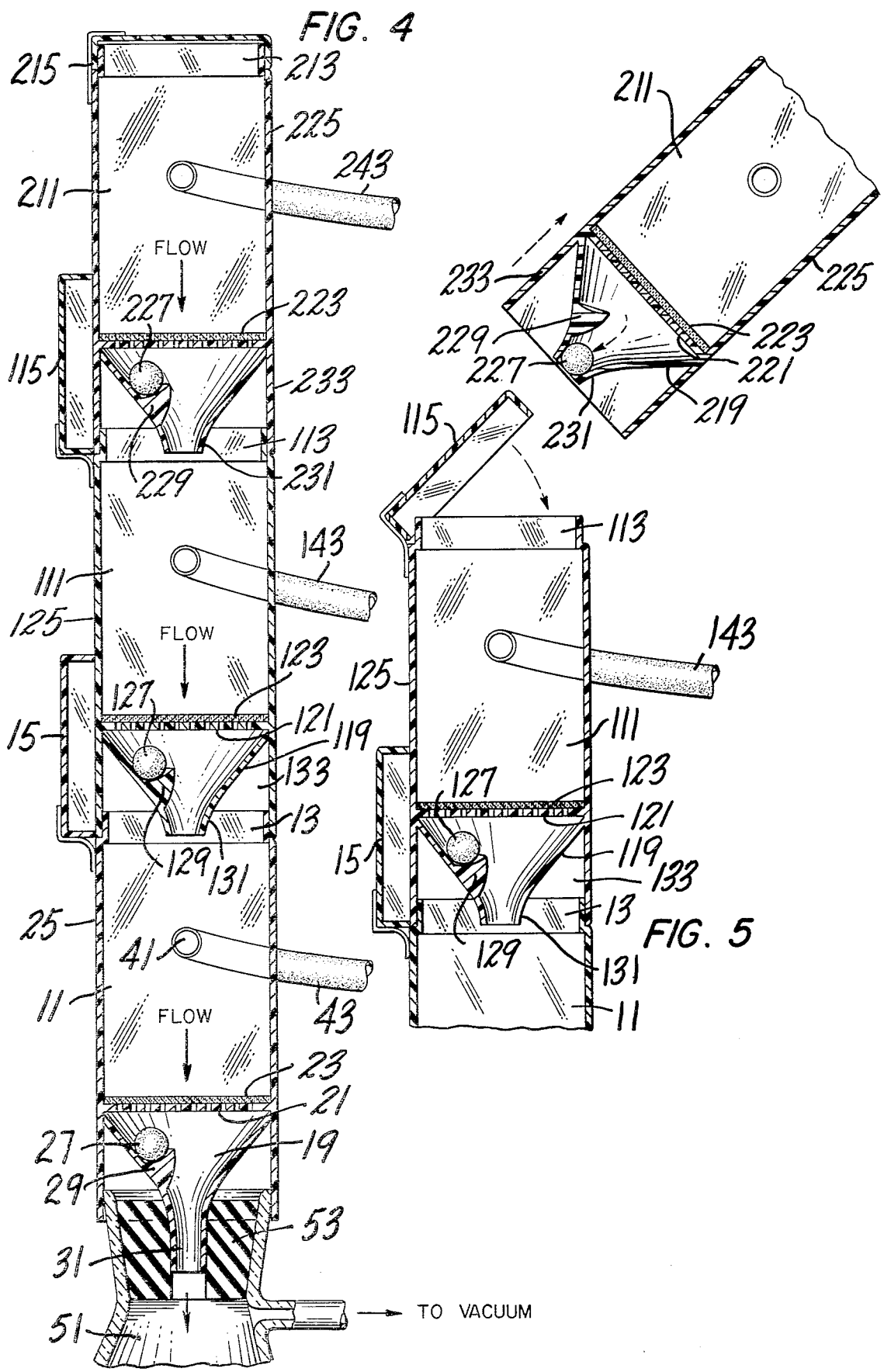

STERILITY TESTING UNIT

BACKGROUND OF THE INVENTION

This invention relates to a disposable unit for testing the sterility of filterable liquids by filtering the liquid using bacteriological membrane filters.

Pharmaceutical and microbiological products such as materials for intravenous or injectable medication, and microbiological media must be sold and used in sterile condition and therefore their sterility must be carefully monitored before distribution and use. Since a large number of tests must frequently be run to ensure that such products are sterile, an inexpensive, efficient, compact and accurate means of testing the sterility of filterable liquids was needed.

Two methods have been used in recent years to carry out sterility testing, the direct method and the membrane filter method which uses a membrane filter to strain the contaminants from the test liquid. In the direct method, a portion of the material to be tested for sterility is innoculated into a medium known to provide optimum conditions for the growth of the specific contaminant organism being tested. The direct method has been abandoned in recent years in favor of the membrane filter method since direct systems are somewhat limited in that they require a specific volumetric to area ratio in order to control the oxygenization of the media. Several sterility test systems using the membrane filter method are now commercially available.

The membrane filter method involves filtering a test liquid through a membrane filter having pores small enough to physically remove any contaminant microorganism from the liquid. The filter is then developed in a growth media to determine if any contaminant microorganisms were present in the test liquid.

The MILLIPORE®[1] filter is an example of a recently developed bacteriological membrane filter. These are filters which consist of stabilized dry, cellulose ester gel membranes about 0.005 inches thick which are supplied as discs or sheets of varying diameters and shapes. These membrane filters are true absolute filters and depend entirely on a sieving action for their effectiveness. In using these membrane filters, it is necessary to know the nature of the organism to be removed. The smallest dimension of the organism to be removed must be greater than the membrane pore size. Tables of characteristic dimension of a wide range of microorganisms and viruses are available in the scientific literature.

[1] MILLIPORE is the registered trademark of Millipore Corporation, Bedford, Mass.

The membrane filter method is conveniently used in liquid sterility test units since the liquids to be tested can easily be filtered using membrane filters, for example Millipore filters. For accurate and reproducible sterility test results, secondary contamination from outside sources must be minimized. For this reason these tests are usually carried out in a clean bench area, for example in a laminar flow hood which eliminates all particles above $0.5\mu$ in diameter. In addition, it is important that handling of the filter membranes be kept to a minimum. The recently developed sterility test systems are designed so that the membrane need not be removed from the test unit in order to be developed.

A liquid sample is tested for sterility in the systems employing the membrane filtration method by filtering the test liquid through the system's test unit. The test unit is rinsed with a suitable sterile solution to remove any residue of the product material retained on the filter and the outlet port is sealed. The unit is filled with a culture medium and the test unit is incubated. Lack of sterility of the test liquid is indicated by turbidity in the medium indicating the presence of contaminants in the liquid tested.

This method is to be contrasted with earlier sterility units and sterility systems in which after the test sample had been filtered the filter membrane was removed from the test unit, divided into sections and each section was incubated in a culture media. This two-step procedure was cumbersome and increased the chances of secondary contamination and is therefore less desirable than systems using single filtration-incubation sterility test units.

Examples of some recently developed systems having filtration-incubation sterility test units herein sometimes referred to as sterility test units or units are described in U.S. Pat. No. 4,036,698 issued July 19, 1977, the Steritest Sterility Testing System marketed by Millipore Corp., the disposable sterile membrane filter unit available from Arthur H. Thomas, Philadelphia, Penn., and the Sartorius Membranfilter Sterility Testing System available from Sartorius Filters, Inc., Cherry Hill, N.J. The test units in these systems overcome many of the drawbacks of previous two-step sterility test units, in that filtration and incubation take place in the same unit, but several problems remain. These commercially available test units lack a convenient method of internally sealing the outlet port of the unit prior to the introduction of the incubation culture medium. In addition, since multiple sterility tests are often run simultaneously, the presently available filtration-incubation sterility test units require considerable hood space since they must be set up side by side.

SUMMARY OF THE INVENTION

It has now been found that an improved disposable filtration and incubation unit for testing the sterility of filterable liquids is provided by applying to prior art devices of the type described, means for stacking one device upon another, and in addition, by providing adjacent the outlet port, means internal to the device for sealing said port, the means capable of being engaged form outside of the device. The filtration and incubation unit of the present invention thus comprises a transparent container having upper and lower ends, an inlet port at the upper end, and outlet port at the lower end, a cap hingeably connected to the upper end and adapted to tightly close the inlet port, a perforated grid having an upper and lower surface positioned within the container, proximate its lower end and secured to the walls thereof to ensure that liquid can pass from the inlet port to the outlet port only through the grid, a membrane filter attached to the upper surface of the grid, a funnel-shaped outlet port located at the lower end of the container attached to the lower surface of the grid to ensure that liquid can pass from the grid only through the outlet port, means positioned within the container between the outlet port and the grid for sealing said outlet port, and means provided at the lower end of said container permitting vertical stacking of the units.

In a preferred embodiment, the means for closing said outlet port includes an inert resilient ball confined within the space between the funnel-shaped tapered outlet port and the grid, and means for restraining said ball at a position remote from said tapered outlet port until closure of said port is desired. The ball when it is released from the restricting means must be large enough to block the tapered outlet port. The ball must have sufficient resiliency to lodge in the tapered outlet port when vacuum is applied to the outlet port of the filtration unit and to remain lodged in the outlet port after the vacuum is released. The means for restraining the ball at a position remote from the outlet port is preferably without limitation a small platform like projection from the upper inner surface of the outlet port the platform having a cup shaped depression in which the ball is retained by gravity.

In an alternate embodiment the means for restraining the ball is an exterior magnet in combination with an inert resilient ball with a piece of iron embedded in it. A suitable inert resilient material for the ball, is, without limitation, a soft neoprene.

Also in the preferred embodiment the means permitting vertical stacking of the units is a housing surrounding the outlet port, the end of which is designed to fit over the inlet port of a second sterility test unit.

The present invention avoids the problems of prior art sterility test units in that the units of the present invention are designed so that one sterility test unit can be stacked on top of another, thus allowing multiple sterility tests to be run in the same amount of space required for one test using currently available equipment. A further improvement of the present invention is that the known sterility test units employ inconvenient methods of sealing the unit prior to introducing the culture media. Both the Millipore and Sartorius systems use an external plug and stopper arrangement to prevent leakage of the developing medium from the unit during incubation. The present invention contains an internal ball device which can be used to conveniently seal the sterility test unit and thus prevent leaks. Since the ball sealing device is internal it is sterilized with the sterility test unit. This feature helps to eliminate problems of secondary contamination which often results from the use of contaminated plugs or stoppers.

Each sterility test unit is placed inside cellophane type packages and sterilized using high energy radiation or other sterilizing techinques such as steam or chemical vapors. The sterilized packages are sealed and stored for use in sterility tests.

The sterile filtration and incubation sterility test units as described above are used either singly or in a stacked array to test the sterility of liquids. In the operation of the sterility units in a stacked array, the first sterility test unit is removed from the sterile package and placed in a clean bench area such as laminar flow hood. All steps in the test are carried out using standard aseptic technique. The outlet port of the first sterility test unit is placed in a standard laboratory filter flask. The flask is attached to a vacuum source and serves as a liquid trap. Although not preferred, the outlet port can be attached directly to a vacuum source such as a water aspirator without the use of an intermediate filter flaks trap. It is preferable that the sterility test unit which is used as the base unit have the tip of the outlet port extend below the housing in order that the outlet port readily fits into the filter flask.

The cap of the first sterility test unit is then lifted. A second sterility test unit is removed from the sterile packaging and placed on top of the first sterility test unit which is already in place on the vacuum flask. The housing surrounding the outlet port of the second sterility test unit fits snugly over the inlet port of the first unit below and the cap of the first unit rests in a perpendicular position against the second unit's outlet port housing. The means for closing the outlet ports in each unit should be in a position remote from the outlet port in order to allow free flow of liquid through the stack of sterility test units. Additional sterility test units can be removed from the packaging and stacked in series as described above if needed.

The cap of the top sterility test unit in the stack remains in an open position and vacuum is drawn through the stack of sterility test units. The first liquid to be tested for sterility is carefully poured through the stack of sterility test units. Bacteria contamination in the test liquid is entrapped on the membrane filter contained within the top unit. When the liquid to be tested has passed through the entire stack of units into the filter trap the stack is flushed with a suitable sterile solution to remove any residue of the test material itself. When the first test liquid has been filtered through the stack of units and they have been suitably rinsed the vacuum is released and the top unit is removed from the stack allowing the cap of the second unit to fall in place over the inlet port. The means for sealing the unit is released and the outlet port is sealed by applying a vacuum to the outlet port. The unit is filled through the inlet port with a suitable culture medium such as thioglycollate, soybean-casein digest medium, sabouraud's or any other culture medium suitable for the growth of microorganisms and the cap is replaced. The culture medium flows through the membrane filter and fills the space between the filter membrane and the sealing means as well as the space above the membrane filter. The culture medium which flows through the membrane and remains in the outlet port does not contain any of the microorganisms being tested for since they are removed by the filter. For this reason, the medium below the filter membrane acts as an internal control for comparison with the medium above the membrane.

The cap of the second sterility test unit is lifted, vacuum is reapplied, and the second liquid to be tested is carefully poured through the stack of sterility test units as described above. The entire procesure is repeated until all the sterility units have been used, removed from the stack and filled with an appropriate culture medium.

The units filled with the culture medium are placed in an appropriate rack, and incubated for an appropriate period at an appropriate temperature. At the end of the incubation period the culture medium is visually examined to determine if there is turbidity in the medium above the filter membrane which indicates contamination. If turbidity appears in the culture medium, samples may be removed for subculture on agar plates to identify the microorganisms. No turbidity should appear in the media below the filter membrane.

The filtration and incubation sterility test units can also be used to run single sterility tests. The same procedure as outlined above is followed except that no stacking or unstacking is necessary.

DESCRIPTION OF THE DRAWINGS

In the drawings:

FIG. 4 is an illustration in sectional view of three sterility test units constructed in accordance with the principles of this invention in a stacked array;

FIG. 5 is an illustration in sectional view of one of the stacked sterility test units being removed from the stack;

DESCRIPTION OF PREFERRED EMBODIMENTS

Figure 1:
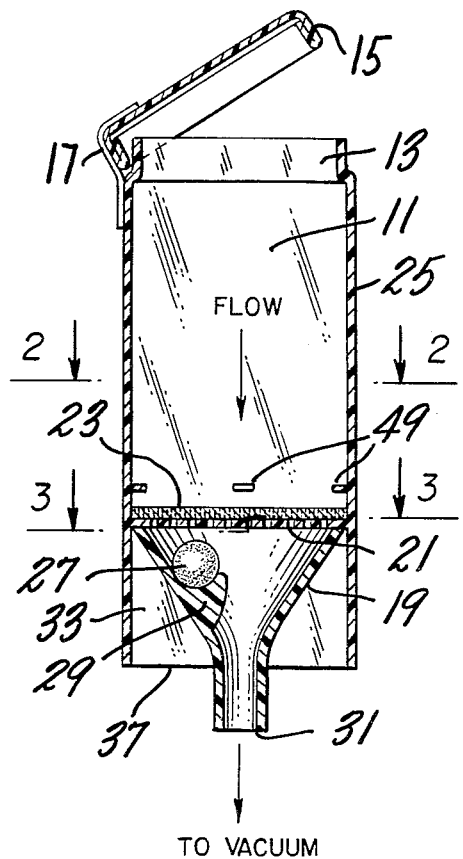
FIG. 1 is an illustration in sectional view of a sterility test unit constructed in accordance with the principles of this invention.
Figure 2:
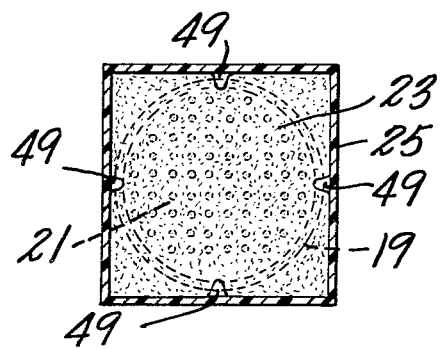
FIG. 2 is a cross section of the sterility test unit of FIG. 1 along lines 2—2.
Figure 3:
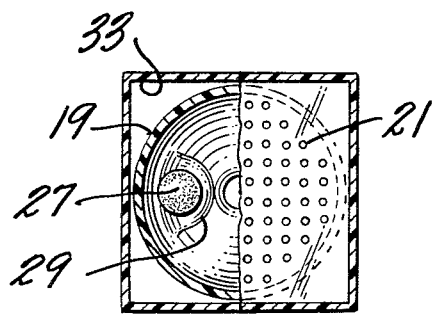
FIG. 3 is a cross section of the sterility test unit of FIG. 1 along lines 3—3 broken away to show the outlet port.

With reference now to the drawings in FIGS. 1-3 a disposable filtration and incubation unit for testing the sterility of filterable liquids is illustrated. The sterility test unit generally indicated at 11 is formed as a block shaped container, preferable of an inexpensive transparent material such as biologically inert polystyrene. At the upper end of the container there is an inlet port 13 provided with a cap 15 which is connected by a hinge 17 to the inlet port 13 and adapted to tightly close the inlet port 13. The hinge 17 for example can be made of semi-rigid nylon reinforced pressure tape or other material which holds the cap when it is lifted in a position somewhat perpendicular to the upper end of the container.

At the lower end of the container 11 there is a tapered outlet port 19 which is preferably funnel shaped. A perforated grid 21 is positioned within the container 11 proximate its lower end to ensure that liquid can pass from the inlet port 13 to the outlet port 19 only through the grid 21. The grid 21 has an upper and lower surface and a membrane filter 23, suitable for removing microorganisms from liquids is attached to the upper surface of the grid 21. The membrane filter 23 substantially covers the full area of the perforated grid 21 and is sealed at its periphery to the grid 21 for example by a biologically inert epoxy cement or by having its edges sandwiched between the wall 25 and the edges of the perforated grid 21. In an alternative embodiment the membrane 23 can be locked in place by projections 49 from the wall 25.

A suitable choice for the membrane filter 23 is a thin (150 $\mu$m) porous membrane composed of biologically inert cellulose esters. The filter preferably is provided with pores 0.45$\mu$ in diameter over its surface. Control of the pores sizes is precise ($\pm 0.02$ $\mu$m) and no microorganisms larger than the largest pore size are passed by the filter. The membrane filter 23 is desirably formed with an annular border in which the surface has been rendered hydrophobic. This may be done for example by covering the border with a solution of xylol and silicone. These types of filters are commercially available from among others Millipore Corporation, Bedford, Mass.

An inert resilient ball 27 is located between the perforated grid 21 and the tip 31 of the outlet port on a platform 29 having a cup shaped depression 55 in which the ball 27 is retained by gravity remote from the outlet port until closure of the outlet port is desired.

In order to make the sterility test unit 11 stackable the outlet port is provided with a housing 33 the end 37 of which is designed to fit over the inlet port 13 of the second sterility test unit as illustrated in FIG. 4.

The use of the sterility test unit in a stackable array of three sterility test units is shown in FIGS. 4-5. This is by way of illustration and is not meant to limit the invention to the use of only three sterility test units. The number of sterility test units which can be vertically stacked are limited only by available vertical space, the stability of the stack and ease of handling.

Prior to assembly, the filtration units are removed from their sterile packages using aseptic technique and placed in an aseptic area such as a laminar flow hood. The ball 27 rests on the platform 29 in the cup shaped depression 55 and should remain in that position until it is necessary to seal the sterility test unit. The outlet port 19 of the bottom unit 11 is seated in the neck of a standard laboratory filter flask 51 fitted with a suitable adaptor 53. The sterility test unit which is used as the base preferably has the tip 31 of the outlet port 19 extending below the housing 33 in order that the outlet port 19 readily fits into the flask. The cap 15 is lifted and the housing 133 of the second sterility test unit 111 is fitted over the inlet port 13 of the first sterility test unit 11. The cap 14 is allowed to rest perpendicularly against the wall 125 of the second unit 111. The cap 115 is lifted from the second unit 111 and the housing 233 of the third unit 211 is seated over the inlet port 113 of the second unit. The cap 215 of the third unit 211 is lifted and a vacuum source is connected to the filter flask and vacuum applied.

The first liquid sample to be tested is poured into the third unit 211. The test liquid passes through units 211, 111 and 11 into the filter flask which serves as a waste trap.

After the first test liquid has passed through the stack each sterility test unit 211, 111, 11 is flushed by pouring a sterile solution such as sterile water through the inlet port of the third sterility test unit 211. This is done to flush the test liquid from the filter surfaces in preparation for incubating the filters in a suitable microorganism growth medium. It is at this point in the test that it is useful to employ a filter membrane 23 with a hydrophobic ring. Without a hydrophobic ring, the test solution absorbed near the edge of the filter membrane 23 is likely not to be completely flushed out and could interfer with the test results. For example if the test solution contained antibiotic material it could inhibit the growth of the test microorganisms and give false results.

After flushing the units, the vacuum is released, the cap 215 is replaced and the top unit 211 is removed from the stack as shown in FIG. 5. The cap 115 of the second unit 111 falls into place to cover the inlet port 113 of the second unit 111. The ball 227 in the third unit 211 is knocked from the cup shaped depression on platform 229 so that it falls into the tapered outlet port 219. The vacuum is applied directly to the tip 231 of the tapered outlet port 219 of the third unit. The vacuum forces the ball 227 into the tip of the outlet port 231 where it remains after the vacuum is released to form a liquid-tight seal. The cap 215 of the third unit is lifted and the unit 211 is filled with a suitable microorganism culture medium for example soybean-casein digest medium. The culture medium flows through the membrane filter 223 and fills the space between the filter 223 and the ball 227 as well as the space above the filter membrane 223. The cap 215 is replaced on the third unit 211 and the unit is incubated under the conditions specified in the United States Pharmacopeia XVIII for the bacteria being tested. For example, soybean-casein digest medium is maintained at a temperature between 20° C. and 25° C. for seven days.

The procedure outlined above is repeated for each of the remaining units 111 and 11.

In the alternative the sterility test can be run without removing the cap from the unit in order to introduce the test liquid or the culture medium. A connector nipple 41 in the wall 25 of the sterility test unit as shown in FIG. 4 is attached to a piece of tubing 43. The tubing 43 can be made of a flexible inert material such as Teflon ®[2] and can be used to introduce liquids directly into the sterility test unit without removing the cap and thereby reduce the chances for additional secondary contamination. The liquid passes through the tubing into the sterility test unit through the action of, for example, a peristaltic action pump. When filtration is completed the top unit is separated from the stack and treated in the same manner as manner as described above except that the culture medium is pumped into the sterility test unit and the hose 43 is clamped to keep it from leaking.

[2]Teflon is the registered trademark of DuPont for polytetrafluoroethylene.

Figure 6:
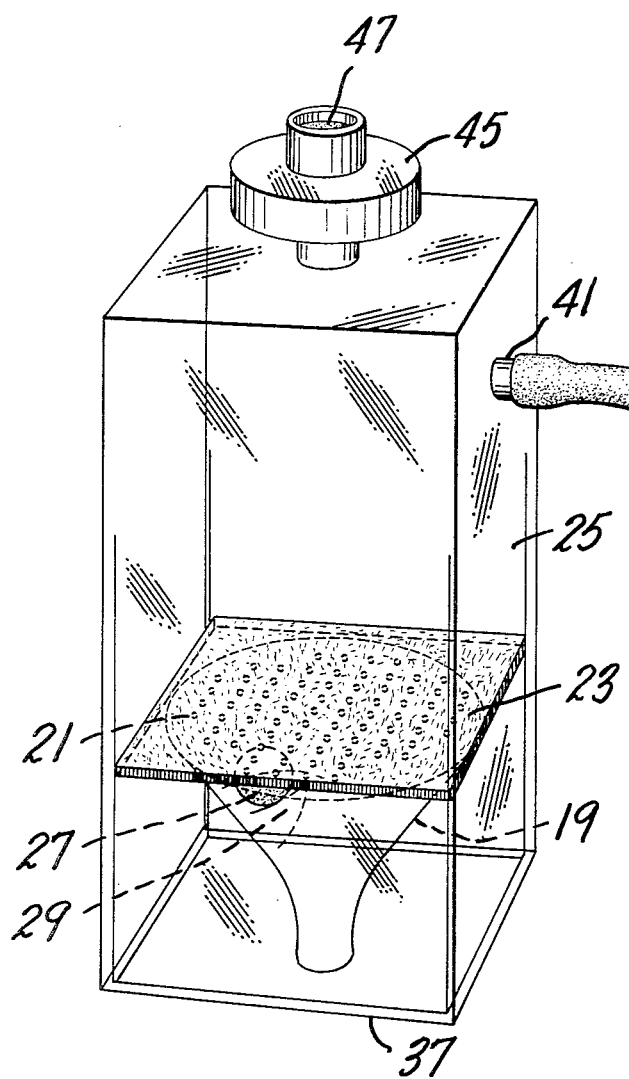
FIG. 6 is an illustration in perspective view of an alternate embodiment of a sterility test unit constructed in accordance with the principles of this invention.
Figure 7:
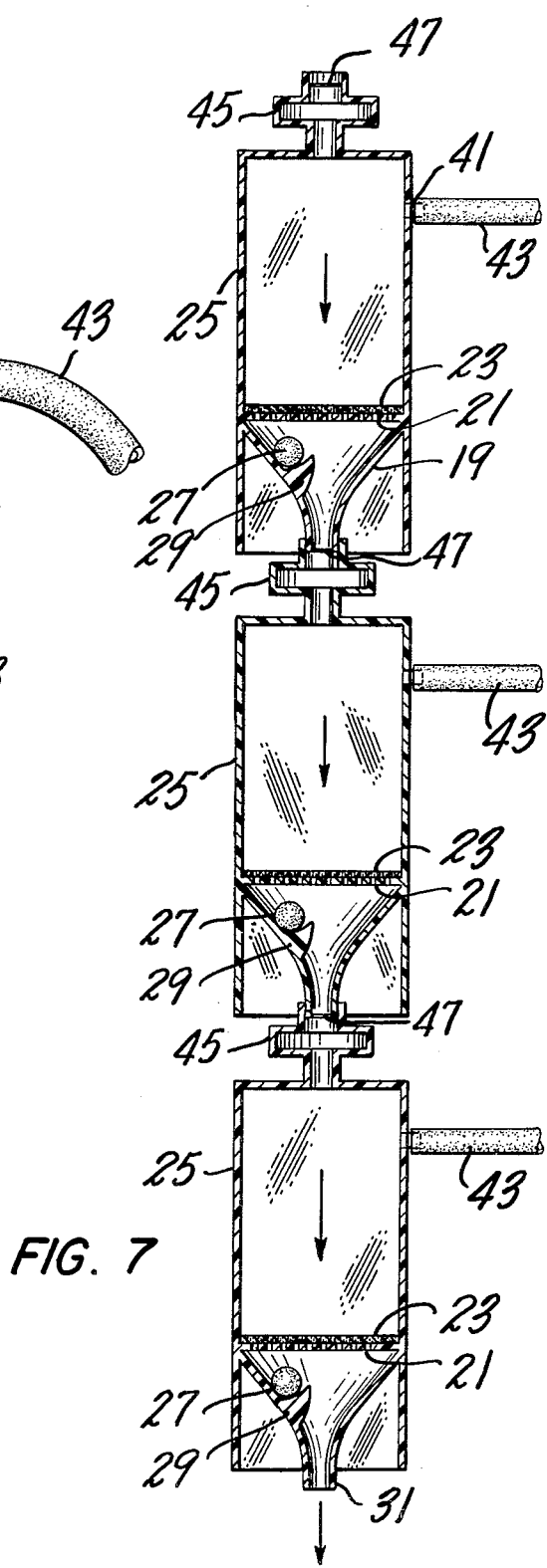
FIG. 7 is an illustration in sectional view of three sterility test units constructed in accordance with this invention as illustrated in FIG. 6 in a stacked array.

An alternate sterility test unit and means of stacking the sterility test unit are shown in FIGS. 6 and 7. The alternate sterility test unit shown in FIG. 6 does not have a cap 15 but rather is closed at the upper end except for a small connector port 45 which leads to the interior of the sterility test unit. The port 45 includes a microporous filter 47 which filters all microorganisms above a specific size from the air flow through the filter. The connector port 45 has an inside diameter slightly larger than the outside diameter of the tip 31 of the outlet port 19 so that the tip 31 of one sterility test unit can fit snugly into the connector port 45 of another test unit. The connector 41 is attached to a piece of tubing 43 and is used to introduce liquids into the sterility test unit as described above.

The unit described in detail above is primarily used for multiple sterility tests of filterable liquids by selecting the proper membrane filter the unit can be used for conducting other filtration operations simultaneously with sterility tests. For example, molecular weight or particle separations can be conducted in the same stack of units as a sterility test. Test units with membrane filters of varying pore sizes are selected and stacked so that the unit with the membrane having the largest pore size is on the top and unit normally used for sterility tests is on the bottom. With this arrangement particulate matter of varying sizes in the test liquid will be separated out by the series of filter membranes. Any contaminating microorganisms will pass through the large pores and be colleced in the bottom most unit which contains the membrane filter suitable for filtering out microorganisms. This technique is particularly useful in testing ophthalmic solution which must not only be tested for sterility but must also be tested for particulate matter of various sizes.

While specific embodiments of the invention have been described, it will be understood that it has other uses and that other materials may in many instances be substituted and the invention should be construed as limited only by the scope of the appended claims.

I claim:

1. A disposable filtration and incubation sterility test unit for testing the sterility of filterable liquids which comprises:
    a transparent container having upper and lower ends,
    an inlet port at the upper end,
    an outlet port at the lower end,
    a cap hingeably connected at the upper end to tightly close the inlet port,
    a perforated grid having an upper and lower surface positioned within the container proximate its lower end and secured to the walls thereof to ensure that liquid can pass from the inlet port to the outlet port only through the grid,
    a membrane filter attached to the upper surface of the perforated grid,
    a funnel-shaped outlet port located at the lower end of the container attached to the lower surface of the grid to assure that liquid can pass from the grid only through the outlet port,
    means positioned within the container between the outlet port and the grid for sealing said port comprising an inert resilient ball confined within the space between the funnel-shaped outlet port and grid and means for restraining the ball at a position remote from the outlet port until closure of the port is desired,
    means provided at the lower end of said container permitting vertical stacking of the filtration and incubation sterility test unit comprising a housing surrounding the outlet.

2. The filtration and incubation sterility test unit as described in claim 1 wherein the means for restraining the ball at a position remote from said outlet port is a platform like projection from the upper inner surface of the outlet port, the platform having a cup shaped depression in which the ball is retained.

3. A stacked array of filtration and incubation sterility test units wherein each unit is as described in claim 1 and wherein the means permitting vertical stacking of one unit is fitted over the inlet port of another sterility test unit.

4. A method of testing for the sterility of liquids comprising the steps of:
    (a) filtering the liquid to be tested through a filtration and incubation sterility test unit, under aseptic conditions said sterility test unit being a transparent container having upper and lower ends, an inlet port at the upper end, an outlet port at the lower end, a cap hingeably connected at the upper end to tightly close the inlet port, a perforated grid having an upper and lower surface positioned within the container proximate its lower end and secured to the walls thereof to ensure that liquid can pass from the inlet port to the outlet port only through the grid, a membrane filter attached to the upper surface of the perforated grid, a funnel-shaped outlet port located at the lower end of the container attached to the lower surface of the grid to ensure that liquid can pass from the grid only through the outlet port, an inert resilient ball confined within the space between the funnel-shaped outlet port and the grid, a means for restraining the ball at a position remote from the outlet port until sealing of the port is desired and means provided at the lower end of said container permitting vertical stacking of the units comprising a housing surrounding the outlet port,
    (b) flushing the unit with a sterile solution,
    (c) sealing the outlet port by knocking the ball into the outlet port and applying vacuum to the outlet port,
    (d) releasing the vacuum, (e) adding a suitable culture medium to the unit, and
(f) incubating the unit under standard conditions for incubating the bacteria being tested.

5. A method of testing for the sterility of liquids comprising the steps of:
(a) stacking a plurality of identical filtration and incubation sterility test units each of said sterility test units being a transparent container having upper and lower ends, an inlet port at the upper end, an outlet port at the lower end, a cap hingeably connected at the upper end to tightly close the inlet port, a perforated grid having an upper and lower surface positioned within the container proximate its lower end and secured to the walls thereof to ensure that liquid can pass from the inlet port to the outlet port only through the grid, a membrane filter attached to the upper surface of the perforated grid, a funnel-shaped outlet port located at the lower end of the container attached to the lower surface of the grid to ensure that liquid can pass from the grid only through the outlet port, an inert resilient ball confined within the space between the funnel-shaped outlet port and the grid, a means for restraining the ball at a position remote from the outlet port until sealing of the port is desired and means provided at the lower end of said container permitting vertical stacking of the units comprising a housing surrounding the outlet port,
(b) filtering the liquid to be tested through the sterility test unit,
(c) flushing the stack of sterility test units with a sterile solution,
(d) removing the top sterility test unit,
(e) sealing the outlet port by knocking the ball into the outlet port and applying vacuum to the outlet port,
(f) releasing the vacuum,
(g) adding a suitable culture medium to the unit,
(h) repeating steps a–g for each sterility test unit, and
(i) incubating the sterility test unit under standard conditions for incubating the bacteria being tested.

* * * * *